(12) United States Patent
Gerber et al.

(10) Patent No.: US 10,758,659 B2
(45) Date of Patent: *Sep. 1, 2020

(54) PERITONEAL DIALYSIS FILTRATE SAMPLING AND ADAPTIVE PRESCRIPTION

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/666,609

(22) Filed: Aug. 2, 2017

(65) Prior Publication Data
US 2018/0043077 A1 Feb. 15, 2018

Related U.S. Application Data

(60) Provisional application No. 62/372,978, filed on Aug. 10, 2016.

(51) Int. Cl.
*A61M 1/28* (2006.01)
*A61M 1/16* (2006.01)
(Continued)

(52) U.S. Cl.
CPC .......... *A61M 1/282* (2014.02); *A61M 1/1609* (2014.02); *A61M 1/1656* (2013.01); *A61M 1/341* (2014.02);
(Continued)

(58) Field of Classification Search
CPC .... A61M 1/282; A61M 1/341; A61M 1/3406; A61M 1/1656; A61M 2205/3379; A61M 2205/3303; A61M 1/1609; G16H 20/17
See application file for complete search history.

(56) References Cited

U.S. PATENT DOCUMENTS 4,747,822 A * 5/1988 Peabody ................. A61M 1/28
128/DIG. 13
4,976,683 A 12/1990 Gauthier
(Continued)

FOREIGN PATENT DOCUMENTS

CN 1273535 11/2000
CN 103619372 3/2014
(Continued)

OTHER PUBLICATIONS

European Search Report for App. No. 17185636.2 dated Jan. 10, 2018.
(Continued)

*Primary Examiner* — Amber R Stiles
(74) *Attorney, Agent, or Firm* — Hahn & Associates

(57) ABSTRACT

The invention relates to systems and methods for optimizing a peritoneal dialysate prescription based on one or more fluid characteristics sensed from a filtrate removed from a patient. The systems and methods include sensors, flow paths, and processors to adjust a peritoneal dialysate prescription and deliver peritoneal dialysis therapy to a patient based on the adjusted prescription. The method can include the steps of removing fluid from a peritoneal cavity of a patient; sampling one or more characteristics of the removed fluid; and adjusting a peritoneal dialysate prescription based on the one or more characteristics of the removed fluid. The system can include a peritoneal dialysate effluent line; at least one concentrate source fluidly connectable to the peritoneal dialysate flow path; and at least one sensor positioned in the peritoneal dialysate effluent line.

20 Claims, 3 Drawing Sheets

(51) Int. Cl.
*A61M 1/34* (2006.01)
*G16H 20/17* (2018.01)

(52) U.S. Cl.
CPC ... *A61M 1/3406* (2014.02); *A61M 2205/3303* (2013.01); *A61M 2205/3379* (2013.01); *G16H 20/17* (2018.01)

(56) References Cited

U.S. PATENT DOCUMENTS

| | | | |
|---|---|---|---|
| 5,032,265 | A | 7/1991 | Jha |
| 5,141,493 | A | 8/1992 | Jacobsen |
| 5,643,201 | A | 7/1997 | Peabody |
| 10,046,100 | B2 | 8/2018 | Burbank |
| 2002/0162778 | A1* | 11/2002 | Peabody ............ A61L 2/022 210/85 |
| 2008/0200866 | A1 | 8/2008 | Prisco |
| 2009/0149776 | A1 | 6/2009 | Adams |
| 2010/0010425 | A1 | 1/2010 | Yu |
| 2010/0137782 | A1 | 6/2010 | Jansson |
| 2010/0312172 | A1 | 12/2010 | Hoffman |
| 2012/0029937 | A1 | 2/2012 | Neftel |
| 2012/0135396 | A1 | 5/2012 | McDevitt |
| 2012/0273354 | A1* | 11/2012 | Orhan ............ A61M 1/284 204/519 |
| 2012/0277551 | A1 | 11/2012 | Gerber |
| 2013/0186759 | A1 | 7/2013 | Lin |
| 2014/0018727 | A1 | 1/2014 | Burbank |
| 2014/0216250 | A1 | 8/2014 | Meyer |
| 2015/0148697 | A1 | 5/2015 | Burnes |
| 2016/0143774 | A1 | 5/2016 | Burnett |

FOREIGN PATENT DOCUMENTS

| | | |
|---|---|---|
| CN | 103717132 | 9/2014 |
| CN | 105008893 B | 10/2015 |
| DE | 3224823 | 1/1984 |
| EP | 0402505 | 12/1990 |
| WO | WO1999006082 | 2/1999 |
| WO | WO2000057935 A1 | 10/2000 |
| WO | WO 20020053211 | 7/2002 |
| WO | WO2009094035 A1 | 1/2008 |
| WO | WO2009154955 A2 | 12/2009 |
| WO | WO 20090154955 | 12/2009 |
| WO | WO 20100002830 | 1/2010 |
| WO | WO2014121161 | 8/2014 |
| WO | WO 20140121169 | 8/2014 |
| WO | WO 20150130205 | 9/2015 |
| WO | WO 20160080883 | 5/2016 |
| WO | WO 20170034452 | 3/2017 |

OTHER PUBLICATIONS

PCTUS2017025858 Written Opinion dated Jun. 29, 2017.
PCTUS2017025876 Written Opinion dated Jun. 29, 2017.
PCT/US2017/025868 International Search Report dated Jun. 29, 2017.
PCT/US2017/025868 Written Opinion dated Jun. 29, 2017.
PCTUS2017025856 International Search Report dated Jun. 29, 2017.
PCTUS2017025876 International Search Report dated Jun. 29, 2017.
European Search Report for App. No. 17185808.7, dated Jan. 2, 2018.
European Search Report for App. No. 17185638.8, dated Dec. 19, 2017.
European Search Report for App. No. 17185810.3, dated Dec. 15, 2017.
European Search Report for App. No. 17185636.2, dated Mar. 27, 2018.
PCTUS20170146199 ISR and written opinion, dated Feb. 19, 2018.
Chinese OA in 201710669452.2 dated Oct. 16, 2019.
Chinese Office Action in App. No. 201710669452.2, dated May 11, 2020.
Chinese Office Action for App. No. 201710669454.1, dated Jul. 3, 2020.

* cited by examiner

PERITONEAL DIALYSIS FILTRATE SAMPLING AND ADAPTIVE PRESCRIPTION

CROSS-REFERENCE TO RELATED APPLICATIONS

This application claims the benefit of and priority to U.S. Provisional Patent Application No. 62/372,978 filed Aug. 10, 2016, the entire disclosure of which is incorporated by reference herein.

FIELD OF THE INVENTION

The invention relates to systems and methods for optimizing a peritoneal dialysate prescription based on one or more fluid characteristics sensed from a filtrate removed from a patient. The systems and methods include sensors, flow paths, and processors to adjust a peritoneal dialysate prescription and deliver peritoneal dialysis therapy to a patient based on the adjusted prescription.

BACKGROUND

Peritoneal Dialysis (PD), including Automated Peritoneal Dialysis (APD) and Continuous Ambulatory Peritoneal Dialysis (CAPD), is a dialysis treatment that can be performed at home, either by a patient alone or with a caregiver. PD differs from Hemodialysis (HD) in that blood is not removed from the body and passed through a dialyzer, but rather a catheter is placed in the peritoneal cavity and dialysate introduced directly into the peritoneal cavity. Blood is cleaned inside the patient using the patient's own peritoneum as a type of dialysis membrane.

The effectiveness of peritoneal dialysis therapy depends on several factors, unique to specific patients. Known systems do not provide any mechanism for optimizing a peritoneal dialysate prescription based on characteristics of peritoneal dialysate filtrate removed from a patient. Solute concentrations, dwell times, cycle number, and other parameters affecting the patient during therapy cannot be controlled with known systems. Further, known systems do not provide any mechanism of adjusting solute concentrations in the dialysate to specific values based on the needs of the patient, and instead only allow a small number of peritoneal dialysate compositions to be used.

Hence, there is a need for systems and methods that can sample peritoneal dialysate filtrate from a patient and determine whether adjustments to a peritoneal dialysate prescription should be made. There is also a need for systems and methods to generate peritoneal dialysate in accordance with any adjusted dialysate prescription. The need includes providing a personalized peritoneal dialysis therapy based on the peritoneal dialysate generated in accordance with the adjusted dialysate prescription.

SUMMARY OF THE INVENTION

The first aspect of the invention relates to a method for adjusting a peritoneal dialysate prescription. In any embodiment, the method can include the steps of removing fluid from a peritoneal cavity of a patient; sampling one or more characteristics of the removed fluid; and adjusting a peritoneal dialysate prescription based on the one or more characteristics of the removed fluid.

In any embodiment, the step of sampling one or more characteristics of the removed fluid can include determining a concentration of one or more solutes in the removed fluid, determining a given volume of fluid removed from the patient, or combinations thereof.

In any embodiment, the solute can be selected from urea, creatinine, glucose, potassium, calcium, magnesium, total protein or combinations thereof.

In any embodiment, the fluid can be from a first peritoneal dialysis cycle.

In any embodiment, the method can include the step of receiving a prior history of a patient, and wherein the peritoneal dialysate prescription is adjusted based on the prior history of the patient.

In any embodiment, the prior history of the patient can include an osmotic agent concentration used in a prior session, an amount of fluid removed in a prior session, a dwell time used in the prior session, and a number of cycles for the prior session.

In any embodiment, the method can include the step of adjusting an osmotic agent concentration, a dwell time, a number of cycles, or combinations thereof, in response to the amount of fluid removed in the prior session.

In any embodiment, the method can include the step of adjusting a number of cycles, a dwell time, or combinations thereof, in response to the solute concentration of the fluid.

In any embodiment, the method can include the step of adjusting a number of cycles, a dwell time, an osmotic agent concentration, or combinations thereof, in response to the net volume of fluid removed from the patient.

In any embodiment, a first amount of fluid can be removed from the patient at a first time and a second amount of fluid can be removed from the patient at a second time; and the step of adjusting the peritoneal dialysate prescription can include adjusting the peritoneal dialysate prescription based on a change in the fluid characteristic between the first time and the second time.

In any embodiment, a first amount of fluid can be removed from the patient at a first time and a second amount of fluid can be removed from the patient at a second time; and the method can include the step of determining a membrane transfer efficiency based on a change in the fluid characteristic between the first time and the second time.

In any embodiment, the fluid characteristic can be a clarity of the fluid, a color spectrum of the fluid, or combinations thereof.

In any embodiment, the step of adjusting the peritoneal dialysate prescription can include adjusting a concentration of an osmotic agent, a number of cycles, a volume of fluid in a cycle, or combinations thereof, based on the membrane transfer efficiency.

In any embodiment, the method can include determining a net volume of fluid removed from the patient from the given volume of fluid removed from the patient.

The features disclosed as being part of the first aspect of the invention can be in the first aspect of the invention, either alone or in combination.

The second aspect of the invention is drawn to a system for adjusting a peritoneal dialysate prescription. In any embodiment the system can include a peritoneal dialysate effluent line; at least one concentrate source fluidly connectable to the peritoneal dialysate flow path; and at least one sensor positioned in the peritoneal dialysate effluent line. In any embodiment, the sensor can sense a volume of fluid removed from a patient. In any embodiment, the sensor can sense a solute concentration of a fluid removed from a patient. In any embodiment, the system can include a processor in communication with the sensor; the processor performing the method of the first aspect of the invention.

In any embodiment, the system can include a peritoneal dialysate generation flow path; the peritoneal dialysate generation flow path having: (i) a water source fluidly connectable to the peritoneal dialysate generation flow path; (ii) one or more water purification modules fluidly connectable to the peritoneal dialysate generation flow path; (iii) a sterilization module fluidly connectable to the peritoneal dialysate generation flow path; and (iv) an integrated cycler fluidly connected to the peritoneal dialysate generation flow path; the processor controlling the movement of fluid from the concentrate source to the peritoneal dialysate generation flow path based on the adjusted peritoneal dialysate prescription.

In any embodiment, the concentrate source can include at least an osmotic agent source and an ion concentrate source.

In any embodiment, the system can include a water source fluidly connectable to a peritoneal dialysate generation flow path; one or more peritoneal dialysate regeneration modules fluidly connectable to the peritoneal dialysate generation flow path; and a sterilization module fluidly connectable to the peritoneal dialysate generation flow path; the processor controlling the movement of fluid from the concentrate source to the peritoneal dialysate generation flow path based on the adjusted peritoneal dialysate prescription.

In any embodiment, the system can include an integrated cycler; the integrated cycler having a pump and either an infusion line and the peritoneal dialysate effluent line, or a combined infusion and effluent line; wherein the infusion line or combined effluent and infusion line is fluidly connected to the peritoneal dialysate generation flow path downstream of the sterilization module; and wherein the peritoneal dialysate effluent line is fluidly connected to the peritoneal dialysate generation flow path upstream of the peritoneal dialysate regeneration module.

The features disclosed as being part of the second aspect of the invention can be in the second aspect of the invention, either alone or in combination.

DETAILED DESCRIPTION OF THE INVENTION

Figure 1:
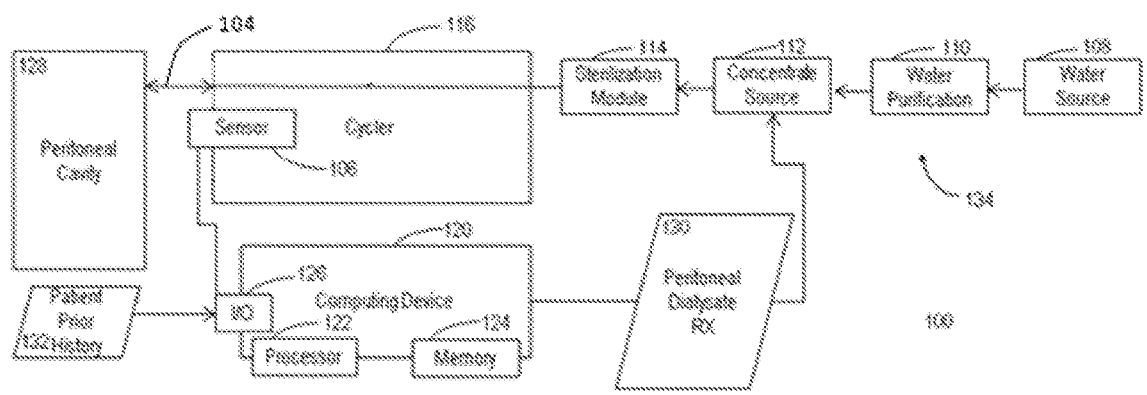
FIG. 1 shows a peritoneal dialysate generation flow path with a sensor and processor for adjusting a peritoneal dialysate prescription.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

An "adjusted peritoneal dialysate prescription" is a peritoneal dialysate prescription that differs in any way from a previously used peritoneal dialysate prescription.

The term "adjusting a peritoneal dialysate prescription" or to "adjust a peritoneal dialysate prescription" refers to changing any parameter of a peritoneal dialysis session, including changing the concentration of one or more solutes, the temperature, the dwell time, and the number of cycles.

A "characteristic of a fluid" or a "fluid characteristic" can refer to any physically observable property of the fluid. In non-limiting examples, the characteristic of the fluid can be the pH of the fluid, the concentration of one or more solutes in the fluid, the pressure, temperature, color, clarity, or any other characteristic of the fluid.

The term "clarity of a fluid" refers to the percentage of light shined on a fluid that passes through the fluid.

The term "color spectrum of a fluid" refers to the wavelength(s) of light absorbed or transmitted by a fluid.

The term "communication" refers to an electronic or wireless link between two components.

The term "comprising" includes, but is not limited to, whatever follows the word "comprising." Use of the term indicates the listed elements are required or mandatory but that other elements are optional and may be present.

A "concentrate source" is a source of one or more solutes. The concentrate source can have one or more solutes with a solute concentration greater than the solute concentration to be used for dialysis. The concentrate in the concentrate source can also be lower than the solute concentration generally used in dialysis for generation of low concentration dialysate.

The terms "concentration" and "solute concentration" refers to an amount of a solute dissolved in a given amount of a solvent.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method.

The terms "control," "controlling," or "controls" refers to the ability of one component to direct the actions of a second component.

The phrase "controlling the movement of fluid" refers to directing fluid through a flow path, container, receptacle, or reservoir of any type.

The term "cycle" or "peritoneal dialysis cycle" refers to the infusion of peritoneal dialysate into a patient, a dwell of the peritoneal dialysate within the peritoneal cavity of the patient, and the removal of the peritoneal dialysate from the peritoneal cavity of the patient. The process of filling and then draining your abdomen can also be seen as an "exchange" of used and clean fluids. However, the number, length, and timing of "cycles" or "exchanges" are non-limiting. For example, Continuous Ambulatory Peritoneal Dialysis (CAPD) and Continuous Cycling Peritoneal Dialysis (CCPD) may occur on different schedules, but the process of filling and then draining the peritoneal cavity can be referred to as "cycles" for both CAPD and CCPD. As such, the term is "cycle" or exchange refers to any particular dialysis schedule or type of dialysis.

The terms "determining" and "determine" refer to ascertaining a particular state of a system or variable(s).

The term "downstream" refers to a position of a first component in a flow path relative to a second component wherein fluid will pass by the second component prior to the first component during normal operation. The first component can be said to be "downstream" of the second component, while the second component is "upstream" of the first component.

The term "dwell time" refers to the amount of time elapsed between infusion of peritoneal dialysate into a patient and drainage of the peritoneal dialysate out of the patient.

The term "first peritoneal dialysis cycle" refers to the first infusion and removal of peritoneal dialysate from a patient in a given session. Depending on the type of peritoneal dialysis treatment received by a patient, the first peritoneal dialysis cycle can be the first cycle of a given day or the first cycle of the night.

A "fluid" is a liquid substance optionally having a combination of gas and liquid phases in the fluid. Notably, a liquid can therefore also have a mixture of gas and liquid phases of matter.

The term "fluidly connectable," "fluidly connected," or "fluid connection" "fluidly connectable" or "fluidly connected" refers to the ability to pass fluid, gas, or mixtures thereof from one point to another point. The two points can be within or between any one or more of compartments, modules, systems, and components, all of any type.

The term "given fluid removed" refers to the volume of fluid removed during a defined time period from the patient.

An "infusion line" is a fluid line for carrying peritoneal dialysate into a body cavity or part of a patient such as a peritoneal cavity. The term "infusion line" can also refer to a combined effluent and infusion line.

An "integrated cycler" is a component for movement of fluid into and out of the peritoneal cavity of a patient, wherein the integrated cycler forms a part of an overall system. For example, the integrated cycler can be contained in a housing with other components used for peritoneal dialysis and be in fluid and electrical connection with desired components.

An "ion concentrate source" refers to a source of one or more ionic compounds. The ion concentrate source can be in water or solid form. The ion concentrate source can further have one or more ionic compounds that are at a higher ion concentration greater than generally used in dialysis. In other words, an ion concentration for each particular ion can be adjusted. The concentration of the ionic compounds in the ion concentrate source can also be lower than the concentration generally used in dialysis for generation of low concentration dialysate.

The term "membrane transfer efficiency" refers to the ability of water or one or more solutes to travel through a semi-permeable membrane, such as the peritoneal membrane of a patient.

The term "net volume of fluid removed" refers to the difference between the volume of dialysate infused into a patient and the volume of used dialysate removed from the patient. The net volume of fluid removed represents the amount of fluid removed from the patient during therapy.

The term "number of cycles" refers to the number of times peritoneal dialysate is infused into and drained from a patient in a given peritoneal dialysis session.

An "osmotic agent" is a substance dissolved in water capable of driving a net movement of water by osmosis across a semi-permeable membrane due to concentration differences of the osmotic agent on each side of the semi-permeable membrane.

An "osmotic agent source" refers to a source of osmotic agents in solid and/or solution form. The osmotic agent source can interface with at least one other module found in systems for dialysis. The osmotic agent source can contain at least one fluid pathway and include components such as conduits, valves, filters or fluid connection ports, any of which are fluidly connectable to each other or to a fluid flow path. The osmotic agent source can either be formed as a stand-alone enclosure or a compartment integrally formed with an apparatus for dialysis for containing an osmotic agent source. The osmotic agent concentration in the osmotic agent source can be lower or higher than the osmotic agent concentration generally used in dialysis for generation of low or high osmotic agent concentration dialysate.

A "patient" or "subject" is a member of any animal species, preferably a mammalian species, optionally a human. The subject can be an apparently healthy individual, an individual suffering from a disease, or an individual being treated for a disease.

The term "peritoneal cavity" refers to a space between the parietal peritoneum and visceral peritoneum of a patient.

"Peritoneal dialysate" is a dialysis solution to be used in peritoneal dialysis having specified parameters for purity and sterility. Peritoneal dialysate is different than dialysate used in hemodialysis, although peritoneal dialysate may be used in hemodialysis.

The term "peritoneal dialysate effluent line" or "effluent line" refers to a fluid connector for removing fluid from a peritoneal cavity of a patient. The term "effluent line" can also refer to a combined infusion and effluent line.

A "peritoneal dialysate generation flow path" is a path used in generating dialysate suitable for peritoneal dialysis.

A "peritoneal dialysate prescription" refers to the set parameters of a peritoneal dialysis session or cycle, including the concentration of one or more solutes in the dialysate, the temperature, the dwell time, and the number of cycles in a session.

The term "peritoneal dialysate regeneration module" refers to a component or components capable of removing waste products from a fluid.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. The cycle can be repeated for several cycles each day or as needed.

The term "positioned" refers to the location of a component.

The term "prior history of a patient" refers to peritoneal dialysis parameters used in treating a patient in one or more previous cycles or sessions, and the results of the peritoneal dialysis treatment. Non-limiting parameters that can be included in the prior history of a patient include an osmotic agent concentration used in a prior session, an amount of fluid removed in a prior session, a dwell time used in the prior session, and a number of cycles for the prior session.

The term "prior session" refers to any peritoneal dialysis session preceding an ongoing peritoneal dialysis session.

The term "processor" as used herein is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "pump" refers to any device that causes the movement of fluids or gases by applying suction or pressure.

The term "receiving" or to "receive" means to obtain information from any source.

The term "removing fluid" refers to flowing fluid out of a container, system, or patient.

The term "sampling" refers to sensing one or more characteristics of a fluid with a sensor.

The term "sensing" or to "sense" refers to determining one or more states of one or more variables in a system.

A "sensor" is a component capable of determining one or more states of one or more variables in a system.

A "solute" is a substance dissolved in, or intended to be dissolved in, a solvent.

A "sterilization module" is a component or set of components to sterilize a fluid by removing or destroying chemical or biological contaminants.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "valve" is a device capable of directing the flow of fluid or gas by opening, closing or obstructing one or more pathways to allow the fluid or gas to travel in a path. One or more valves can be positioned to accomplish a desired flow by a "valve assembly."

The term "volume of fluid removed from the patient" refers to the amount of fluid drained or pumped out of the peritoneal cavity of a patient during a peritoneal dialysis cycle.

The term "water purification module" refers to a component or components capable of removing biological or chemical contaminants from water.

The term "water source" refers to a source from which potable water can be obtained.

Peritoneal Dialysis Filtrate Sampling and Adaptive Prescription

FIG. 1 is a non-limiting flow path of a peritoneal dialysis system 100 having an integrated cycler 116 for delivering peritoneal dialysis therapy to a patient. The integrated cycler 116 includes a combined effluent and infusion line 104 for infusing peritoneal dialysate into a peritoneal cavity 128 of a patient, and for removing fluid from the peritoneal cavity 128 of the patient. The combined effluent and infusion line is referred to herein as simply an "effluent line." The integrated cycler 116 can divert fluid into and of the patient. Alternatively, separate effluent and infusion lines can be used for infusing peritoneal dialysate into and removing peritoneal dialysate from the peritoneal cavity of the patient. The effluent line 104 includes at least one sensor 106 for sampling fluid removed from the peritoneal cavity 128 of a patient to adjust a peritoneal dialysate prescription 130. The system 100 can also include a peritoneal dialysate generation flow path 134 for generating peritoneal dialysate to be delivered to the patient. The peritoneal dialysate generation flow path 134 can include pumps, valves, and sensors, for controlling the peritoneal dialysate generation.

The peritoneal dialysate generation flow path 134 can include a water source 108, one or more water purification modules 110, one or more concentrate sources 112, a sterilization module 114, and the integrated cycler 116. The water source 108 can be a non-purified water source, such as tap water, wherein the water from the water source 108 can be purified by the system. A non-purified water source can provide water without additional purification, such as tap water from a municipal water source, water that has undergone level of purification, but does not meet the definition of "purified water" provided, such as bottled water or filtered water. The water source can contain water meeting the WHO drinkable water standards provided in *Guidelines for Drinking Water Quality*, World Health Organization, Geneva, Switzerland, 4th edition, 2011. Alternatively, the water source 108 can be a source of purified water, meaning water that meets the applicable standards for use in peritoneal dialysis without additional purification. The system pumps water from the water source to the water purification module 110 to remove chemical contaminants in the fluid in preparation for creating dialysate. The water purification module 110 can be a sorbent cartridge containing anion and cation exchange resins and/or activated carbon.

The system can pump the fluid to a sterilization module 114 for sterilization of the peritoneal dialysate prior to infusion into the patient. The sterilization module 114 can include one or more of a first ultrafilter, a second ultrafilter, and a UV light source, or any combination thereof. The sterilization module can be any component or set of components capable of sterilizing the peritoneal dialysate.

The concentrate sources 112 can contain one or more solutes for generation of the peritoneal dialysate from purified water. The concentrates in the concentrate source 112 are utilized to create a peritoneal dialysis fluid that matches a dialysis prescription. A concentrate pump (not shown) in communication with the processor or computing unit controls the movement of concentrates from the concentrate sources 112 into the peritoneal dialysate generation flow path 134. Table 1 provides non-limiting exemplary ranges of commonly used components of peritoneal dialysate. One of skill in the art will understand that alternatives to the components listed in Table 1 can be used. Other osmotic agents can be used in addition to, or in place of, the dextrose, including glucose, icodextrin or amino acid solutions, including dialysate with multiple osmotic agents. Although the sources of sodium, calcium, and magnesium listed in Table 1 are chloride salts, other sodium, magnesium, and calcium salts can be used, such as lactate or acetate salts. Peritoneal dialysate may also contain buffers for maintaining pH of the peritoneal dialysate. Exemplary, non-limiting examples of suitable buffers include bicarbonate buffer, acetate buffer or lactate buffer. Although not generally used in peritoneal dialysis, potassium chloride can be used for hypokalemic patients who don't receive sufficient potassium through diet. The concentrate sources 112 can include any number of concentrates combined or in separate concentrate sources. For example, one or more osmotic agent sources can be included in addition to a single ion concentrate source. Alternatively, multiple ion concentrate sources can be used with each ion concentrate in a separate concentrate source. Any combination of concentrates in any number of concentrate sources can be used with the invention.

TABLE 1

| Component | Concentration |
| --- | --- |
| Sodium chloride | 132-134 mmol/L |
| Calcium chloride dehydrate | 1.25-1.75 mmol/L |
| Magnesium chloride hexahydrate | 0.25-0.75 mmol/L |
| Sodium Lactate | 35-40 mmol/L |

TABLE 1-continued

| Component | Concentration |
|---|---|
| Dextrose (D-glucose) monohydrate | 0.55-4.25 g/dL |
| pH | 5-6 |
| Osmolality | 346-485 (hypertonic) |

The water source 108, water purification module 110, concentrate source 112, and sterilization module 114 can be fluidly connectable to the integrated cycler 116 for immediate delivery of the generated peritoneal dialysate to the patient. Alternatively, a peritoneal dialysate reservoir (not shown) can be included to collect the generated peritoneal dialysate for later use. One or more processors 122 which can be part of a larger computing device 120, can control the movement of fluid from the concentrate source 112 to the peritoneal dialysate generation flow path 134 based on a peritoneal dialysate prescription 130. The concentrate sources can infuse each particular concentrate to provide an infused ion concentration that is lower than a prescribed amount for a particular patient. One desired outcome can be to provide a concentration for a particular ion that is lower than a patient's pre-dialysis ion concentration. Additionally, if multiple ion sources are to be delivered by a concentrate source, the present system can selectively dilute a desired ion while maintaining concentration levels for other ions. Hence, the present invention can avoid adjusting down every ion insofar as an added diluent may adversely affect concentrations of ions already in a normal range.

As described, one or more sensors 106 can be positioned in the peritoneal dialysate effluent line 104, the peritoneal dialysate generation flow path 134, or in both the peritoneal dialysate effluent line 104 and the peritoneal dialysate generation flow path 134. If a separate infusion line is used, the sensor 106 can be included in the infusion line. The one or more sensors 106 can be separate sensors or a combined sensor positioned along both the peritoneal dialysate effluent line 104 and the peritoneal dialysate generation flow path 134, or combinations thereof. The one or more sensors 106 can be placed at various locations along the peritoneal dialysate effluent line 104 and the peritoneal dialysate generation flow path 134, including within or between the cycler 116, the water source 108, the water purification module 110, the concentrate source 112, and the sterilization module 114, or between the cycler 116 and the peritoneal cavity 128.

The one or more sensors 106 can include a flow sensor to measure a volume of fluid infused into and removed from a patient, a solute concentration sensor, such as a conductivity sensor, to measure a solute concentration of the fluid removed from the patient, a refractive index sensor to measure glucose or other osmotic agent concentration in the fluid removed from the patient, and pressure sensor to measure a pressure of fluid removed from a patient. Any combination of sensors can be used, as described. Any of the sensors can be included on the combined effluent and infusion line, or alternatively, the same sensors can be included on separate effluent and infusion lines. Including the same sensors on the delivery line of dialysate into the patient as in the effluent line allows the system to determine changes between the infused fluid and the removed fluid.

The computing device 120 can include the one or more processors 122, memory 124, and one or more input/output interfaces 126. The memory 124 can be in communication with the processor 122 and store instructions that when executed perform the methods of the present invention. The input/output interfaces 126 can include an input port to receive prior history 132 of the patient, information from the one or more sensors 106, and any other information that can be entered by a patient or health care professional. The input/output interface 126 can also have an output interface to output an adjustment to the peritoneal dialysate prescription. The processor 122 can be in communication with the at least one sensor 106. As with all features of the present application, intervening components (such as the input/output interface 126) can be present between the processor 122 and the sensor 106. The computing device 120 can be a stand-alone device independent of the integrated cycler 116, or can be a part of the integrated cycler 116. The computing device 120 can be a remote device in network communication with the sensor 106, such as via the Internet.

Figure 2:
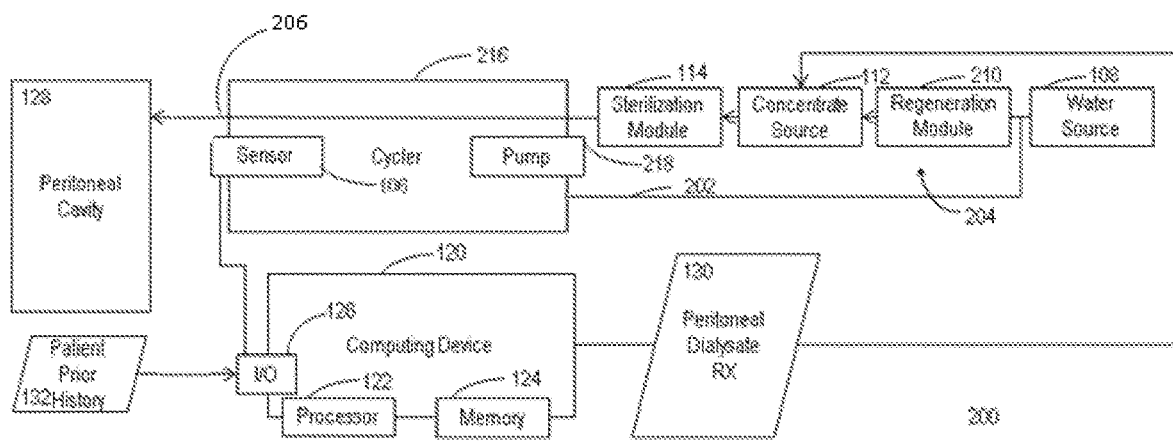
FIG. 2 shows a peritoneal dialysate generation flow path with a sensor and processor for adjusting a peritoneal dialysate prescription, and including a peritoneal dialysate regeneration module.

FIG. 2 shows an alternative system 200 for sampling fluid of a peritoneal cavity 128 of a patient to adjust a peritoneal dialysate prescription 130. A difference between system 200 and system 100 is the provision of a peritoneal dialysate regeneration module 210. A discussion of features similar to the features of system 100 is omitted in the interest of brevity.

The system 200 can include a combined peritoneal dialysate effluent and infusion line 206, referred to herein as an effluent line, a peritoneal dialysate generation flow path 234, and an integrated cycler 216. The integrated cycler 216 can include a pump 218, and the peritoneal dialysate effluent line 206 and a regeneration line 202 fluidly connected to the regeneration module 210. The effluent line 206 can be fluidly connected to the peritoneal dialysate generation flow path 204 downstream of the sterilization module 114. The regeneration line 202 can be fluidly connected to the effluent line 206 within the cycler 216 and the peritoneal dialysate generation flow path 204 upstream of the peritoneal dialysate regeneration module 210. The regeneration module can be any component or set of components capable of removing waste products and other solutes from the dialysate.

The systems illustrated in FIGS. 1-2 include a peritoneal dialysate generation flow path with an integrated cycler. One of skill in the art will understand that the systems can be adapted for use with a non-integrated cycler by removing samples of filtrate from the non-integrated cycler and providing feedback to the computing unit based on the sensed fluid characteristics.

One of ordinary skill in the art will recognize that multiple characteristics of fluid sampled by systems 100, 200 of FIGS. 1 and 2 can be analyzed to determine adjustments to the peritoneal dialysate prescription 130. Table 2 contains illustrative examples of characteristics and possible adjustment.

TABLE 2

| Characteristic of Fluid | Possible Adjustments |
|---|---|
| Concentration of solute (e.g., urea, glucose, potassium, or combinations of urea, glucose, potassium and urea) | Dwell time, number of cycles, volume of dialysate infused |
| Net or given volume of fluid removed from the patient | Dextrose, dwell time, number of cycles, osmotic agent concentration |
| Glucose or dextrose concentration | Dwell time |
| Conductivity | Dwell time |
| Peritoneal membrane transfer efficiency | Dialysate composition, number of cycles, volume |

The operation of the systems 100, 200 of FIGS. 1 and 2 is now described with reference to FIGS. 3 and 4 which are schematic representations of computerized methods for adjusting a peritoneal dialysate prescription 130 based on sampled filtrate removed from the peritoneal cavity 128 of a patient.

Figure 3:
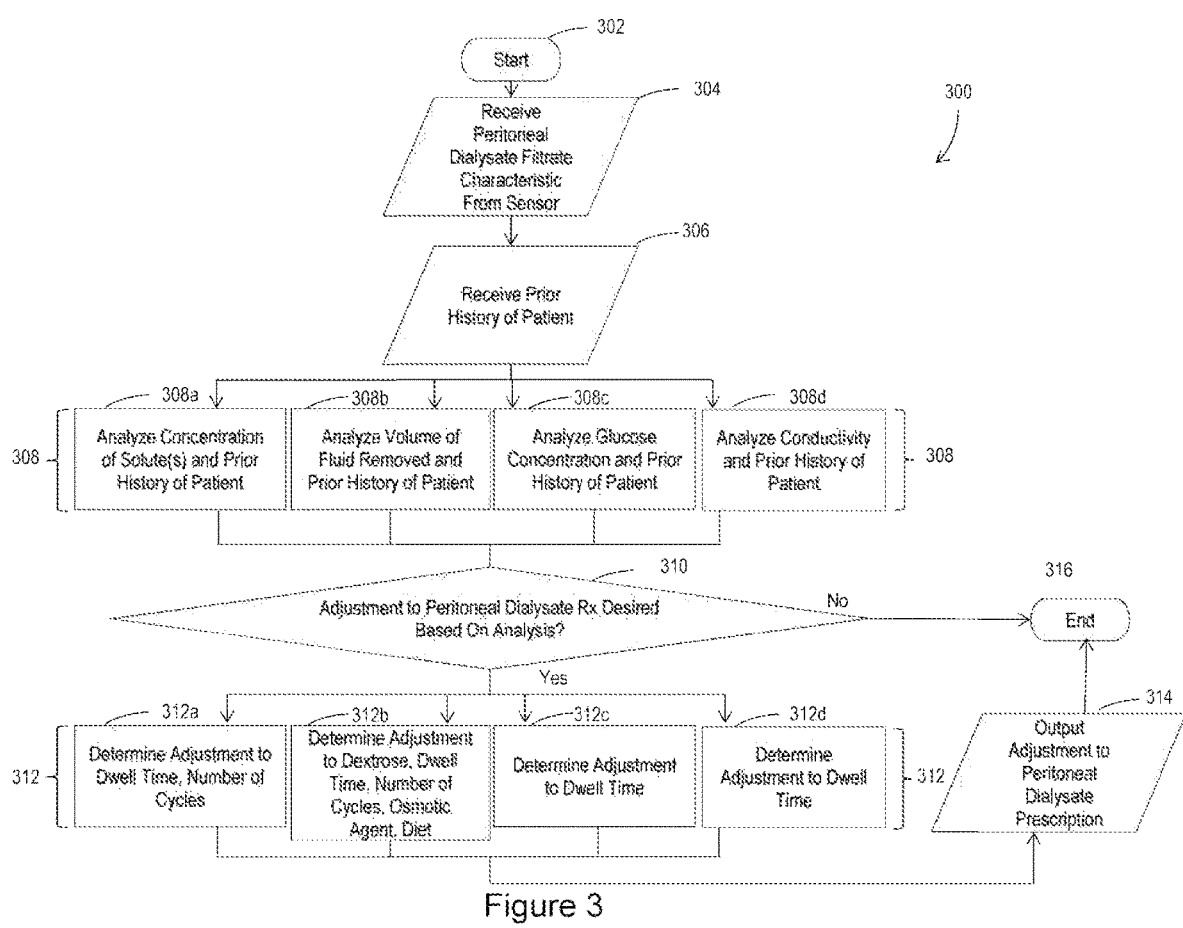
FIG. 3 is a flow chart illustrating a method of adjusting a peritoneal dialysate prescription based on sampled filtrate.

FIG. 3 is a flowchart of a computerized method 300 for adjusting a peritoneal dialysate prescription based on sampled peritoneal dialysate filtrate. The method 300 can begin in operation 302. Fluid can be removed from a peritoneal cavity of a patient. The fluid can be removed through a peritoneal dialysate effluent line including at least one sensor.

In operation 304, input representing one or more characteristics of the fluid can be received into the computing device from the sensors sampling the filtrate in the effluent line of the cycler. For example, a concentration of one or more solutes in the fluid can be measured using a solute concentration sensor or a conductivity sensor. The solute can be urea, glucose, potassium, dextrose or combinations of urea, glucose, dextrose, and potassium. Similar to measuring the concentration of a solute using a solute concentration sensor, a net volume of the fluid removed from the peritoneal cavity, a glucose or other osmotic agent concentration, and conductivity can be measured using a flow sensor, a refractive index sensor, and a conductivity sensor, respectively. The net volume of fluid removed from the patient can be determined from the difference between the volume of dialysate infused into the patient and the volume of dialysate removed from the patient at the end of the cycle. One of skill in the art will understand that alternative or additional sensors can be used in addition to the sensors listed. Any sensor known in the art capable of determining one or more fluid characteristics of the filtrate is within the scope of the invention.

Optionally, in step 306, input representing prior history of the patient can be received into the computing device through the input/output interface. For example, the prior history of the patient can include one or more of an osmotic agent concentration used in a prior session, an amount of fluid removed in the prior session, a dwell time used in the prior session, and a number of cycles for the prior session. The prior history of the patient can be manually input into the computing device, or can be automatically received by the computing device from electronic medical records of the patient.

In operation 308, the input representing one or more characteristics received in operation 304 and optionally the prior history of the patient received in operation 306 can be analyzed. Multiple instances of operation 308 are depicted in FIG. 3. For example, in operation 308a, a concentration of solute(s) and the prior history of the patient can be analyzed. Alternatively, in operation 308b, a net or given volume of fluid removed and the prior history of the patient can be analyzed. Alternatively, in operations 308c and 308d, a glucose or other osmotic agent concentration and conductivity, respectively, and the prior history of the patient can be analyzed. Any combination fluid characteristics of the sampled filtrate can be analyzed in step 308.

In operation 310, a determination is made of whether an adjustment to the peritoneal dialysate prescription is recommended based on the analysis performed during operation 308. For example, if a net or given volume of fluid removed from the patient is measured using a flow sensor, the input characteristic of net or given volume of fluid removed and the input prior history indicating a net or given volume of fluid removed in the prior session can be analyzed in operation 308. If the sensed net or given volume removed meets a condition relative to the prior history, then a determination can be made in operation 310 that an adjustment to the peritoneal dialysate prescription is desirable. For example, if the net or given volume of fluid removed from the patient is low relative to the prior history or target, then an adjustment to the peritoneal dialysate prescription increasing the concentration of dextrose in the peritoneal dialysate can be recommended. The processors and systems illustrated in FIGS. 1-2 can automatically adjust the amount of osmotic agent added from the concentrate source to provide a peritoneal dialysate with a higher osmotic agent concentration. If the net or given volume of fluid removed from the patient is high relative to the prior history or target, the osmotic agent concentration, could be lowered, the cycle time could be shortened, or the number of cycles could be reduced. Alternatively, the system can determine that the dwell time used in the peritoneal dialysis session should be increased to remove additional fluid from the patient.

The concentration of one or more solutes in the filtrate can also analyzed in operation 308. For example, a urea sensor can provide the urea concentration in the filtrate. A high urea concentration could indicate that additional therapy is required for the patient. The system can increase the number of cycles or increase the dwell time to remove the additional urea in the patient. Conversely, a drop in urea concentration relative to historical levels for the patient could indicate a poor clearance across the peritoneum. Other solutes that can be analyzed as above include creatinine, ureic acid, B-2 microglobulin. A UV-Visible spectrophotometric sensor or other suitable sensor can be used for analysis of solutes. In some cases one or more reagents may be added to the dialysate sample to improve specificity or detection of the analyte of interest. A conductivity sensor or ion-selective electrode can determine the concentrations of potassium, calcium and/or magnesium in the filtrate. Alternatively, assay technology similar to a blood analyzer could be used. The sensors can be external to the patient and part of the system. A low level of potassium, calcium, and/or magnesium could be indicative of poor clearance across the peritoneum. The composition of the peritoneal dialysate can be adjusted to decrease the amount of potassium, calcium, and/or magnesium in the dialysate to remove additional solutes from the patient. The operation could be repeated after making the composition change to determine whether further adjustments are needed. A refractive index sensor can be used to measure the glucose or other osmotic agent in the filtrate. The osmotic agent concentration can be used to optimize the dwell time or the number of cycles in a session. A low osmotic agent concentration could indicate equilibrium with the patient and that a new cycle should begin. In subsequent peritoneal dialysis sessions, the dwell time could then be reduced. In a preferred embodiment, the filtrate sampling to determine solute concentration is performed in the first peritoneal dialysis cycle of a session. The first peritoneal dialysis cycle, as used herein, refers to the first cycle of the day or night for the patient, and can depend on the type of peritoneal dialysis received. The first peritoneal dialysis cycle tends to baseline the patient for the session and is mostly useful to set session parameters and to monitor longer term health of the patient and peritoneum. The first peritoneal dialysis cycle will give initial state of patient. However, subsequent cycles could also be used for determining clearance and adjusting the peritoneal dialysate prescription.

One of ordinary skill in the art will recognize that the analysis of operation 308 can be performed in a number of ways. For example, rather than determining if the input characteristic meets a condition relative to the prior history, a determination can be made whether the input fluid characteristic fails to meet a condition relative to the prior history. As another example, a determination can be made whether the prior history meets or fails to meet a condition relative to the input characteristic. Any variations are intended to be considered as equivalent approaches under the general concept of operation 308. If in operation 310 a determination is made that an adjustment to the peritoneal dialysate is not recommended, the method can proceed to operation 316 and end. The same peritoneal dialysate prescription can be used in future peritoneal dialysis sessions.

If in operation 310 a determination is made that an adjustment to the peritoneal dialysate is recommended, the method can proceed to operation 312. In operation 312, an adjustment to the peritoneal dialysate prescription can be determined based on the analysis of the input relative to the prior history performed during operation 308. Multiple instances of operation 312 are depicted in FIG. 3. For example, in operation 312a, an adjustment to one or more of a dwell time and a number of cycles can be determined. Alternatively, in the net volume of fluid removed from the patient example, a determination can be made in operation 312b that adjustment should be made to one or more of dextrose, a dwell time, a number of cycles, an osmotic agent concentration. Alternatively, in operation 312c, an adjustment to cycle duration can be determined. In the conductivity example, a determination can be made in operation 312d that adjustment should be made to dwell time.

In operation 314, the adjustment to the peritoneal dialysate prescription determined in operation 312 can be output via the input/output port illustrated in FIGS. 1-2. For example, the adjustment to the peritoneal dialysate prescription can be output through the input/output port to a display (not shown). The adjustment to the peritoneal dialysate prescription can be output through the input/output port via an electronic or printed communication to a prescribing physician, such as via email or a transmitted report. Alternatively, or additionally, the adjustment to the peritoneal dialysate can be implemented automatically via the system. For example, the processor can be in communication with the concentrate source and can control the movement of fluid from the concentrate source to the peritoneal dialysate generation flow path based on the adjusted peritoneal dialysate prescription. After the outputting of the adjustment to the peritoneal dialysate prescription in operation 314, the method can end in operation 316.

One of ordinary skill in the art will recognize that the method 300 can be a repeating method thereby providing continual monitoring of peritoneal dialysate filtrate samples. In such an embodiment, some or all of the operations of method 300 can be repeated in one or more loops without the method 300 ending in operation 316. The repeated operation of method 300 allows the system to create trends which can be analyzed to determine the overall health of the patient and long term adjustments to the prescription. For example, a decrease in the net volume of fluid removed from the patient trending over time may indicate a health problem with the peritoneum of the patient.

Figure 4:
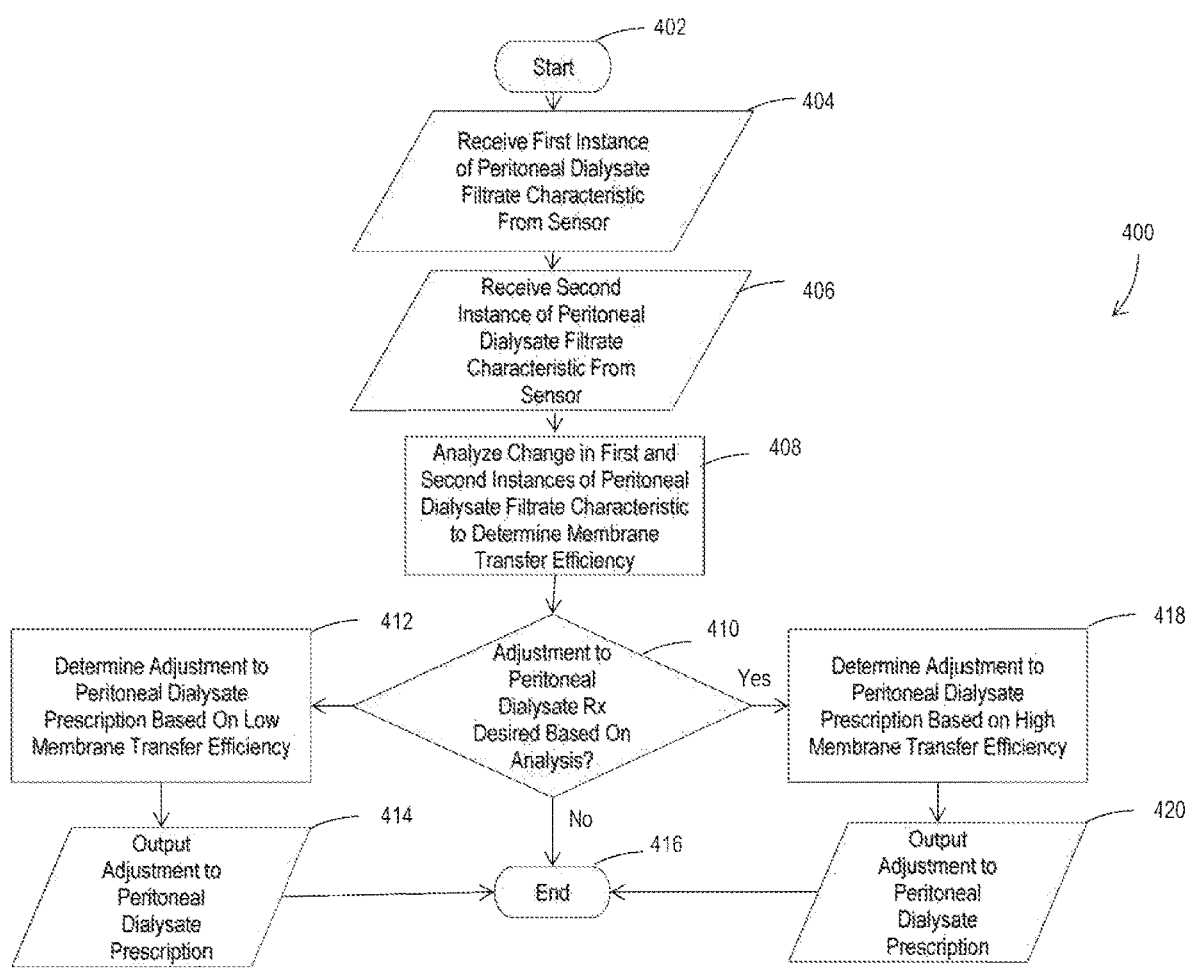
FIG. 4 is a flow chart illustrating a method of adjusting a peritoneal dialysate prescription based on changes to a peritoneal dialysate filtrate over time.

FIG. 4 is a flowchart of a computerized method 400 for adjusting a peritoneal dialysate prescription based on a sampled peritoneal dialysate filtrate fluid. The method 400 can begin at operation 402. A first amount of fluid can be removed from a peritoneal cavity of a patient at a first time. The fluid can be removed through a peritoneal dialysate effluent line including at least one sensor. A second amount of fluid can be removed from the peritoneal cavity of the patient at a second time and a fluid characteristic of each sample of peritoneal dialysate determined.

In operation 404, input representing one or more characteristics of the fluid removed at the first time can be received into the computing device from the sensor. One or more characteristics of the fluid can be sampled using the sensor. For example, a first instance of a net or given volume of fluid removed from the peritoneal cavity can be measured using a flow sensor. In operation 406, input representing one or more characteristics of the fluid removed at the second time can be received into the computing device from the sensor. For example, a second instance of a net or given volume of the fluid removed from the peritoneal cavity can be measured using the flow sensor.

In operation 408, the input representing the one or more characteristics of the removed fluid at the first and second times can be analyzed to determine a membrane transfer efficiency of the peritoneum of the patient. In operation 410, a determination is made whether an adjustment to the peritoneal dialysate prescription is recommended based on the membrane transfer efficiency of the peritoneal cavity. The second instance of the net or given volume of fluid removed from the patient can be compared to the first instance of the net or given volume of fluid removed from the patient to determine the membrane transfer efficiency. The membrane transfer efficiency is a function of the net or given fluid removed from the patient in either a cycle or a session. Membrane transfer efficiency is also a function of the PD fluid dextrose, volume removed in a specific session, dwell time, cycle number, and other factors. One of skill in the art will understand that the factors in determining the membrane transfer efficiency can be determined using the systems and then calculated. If in operation 410 a determination is made that an adjustment to the peritoneal dialysate is not recommended, the method can proceed to operation 416 and end. A baseline membrane transfer efficiency for a patient can be created and trended. The trend of membrane transfer efficiency can be used by a health care professional to determine any changes in the peritoneum health of the patient.

If in operation 408 a determination is made that the membrane transfer efficiency is low, then a determination can be made in operation 410 to adjust the peritoneal dialysate prescription based on the low membrane transfer efficiency and the method 400 can proceed to operation 412. In operation 412, an adjustment to the peritoneal dialysate prescription can be determined based on the analysis determining membrane transfer efficiency. For example, one or more of increasing a number of dwell cycles, increasing a volume of fluid to be introduced via the infusion line, and increasing dextrose can be determined to be recommended in response to a low membrane transfer efficiency. In operation 414, the adjusted peritoneal dialysate prescription determined in operation 412 can be output via the input/output port as described. After outputting the adjustment to the peritoneal dialysate prescription in operation 414, the method can end in operation 416.

If in operation 408 a determination is made that the membrane transfer efficiency is high, then a determination can be made in operation 410 to adjust the peritoneal dialysate prescription based on the high membrane transfer efficiency and the method 400 can proceed to operation 418. In operation 418, an adjustment to the peritoneal dialysate prescription can be determined based on the analysis determining membrane transfer efficiency. For example, one or more of decreasing a number of dwell cycles, decreasing a volume of fluid to be introduced via the infusion line, and decreasing dextrose or osmotic agent concentration can be determined to be recommended. In operation 420, the adjustment to the peritoneal dialysate prescription determined in operation 418 can be output via the input/output port. After outputting the adjustment to the peritoneal dialysate prescription in operation 420, the method can end in operation 416.

As described, a baseline trend of membrane transfer efficiency can be created, and the calculated membrane transfer efficiency compared to the baseline. The baseline can include any amount of time measurements over the course of therapy, including a running average of the previous 2-4 weeks. The calculated membrane transfer efficiency can be compared to the baseline, and the dialysate prescription adjusted if the calculated membrane transfer efficiency differs from the baseline by a predetermined amount. The predetermined amount can be any value, including a value less than 90% of the baseline or greater than 110% of the baseline. The membrane transfer efficiency can be calculated by changes in solute concentration of the filtrate, or changes in the amount of fluid removed from a patient. For example, if 1 L of dialysate is infused into a patient and 1.2 L removed, then the net fluid removed is 0.2 L. The amount of fluid removed based on a given osmotic agent concentration can be compared to the trend to determine changes in membrane transfer efficiency.

The filtrate sampling can also be used to optimize a peritoneal dialysis cycle. For example, a refractive index sensor can be included to monitor glucose or other osmotic agent concentration in filtrate removed from the patient at multiple points in time within a cycle. A lower level of an osmotic agent would provide an indication that the peritoneal dialysate in the peritoneal cavity of the patient should be changed. Thus, adapting the dwell time based on osmotic agent concentration which is correlated with clearance. Alternatively, a conductivity sensor could be used. When conductivity reaches a plateau, equilibration of PD fluid with the patient would be indicated, and a new cycle started.

The peritoneal dialysate filtrate can be sampled across multiple peritoneal dialysis sessions to provide a trend. Fluid characteristics that can be trended on either an acute or multisession basis include the fluid pressure in the peritoneum of the patient, and the net volume of fluid removed from the patient. The fluid characteristics can be used for determining the health of the catheter and peritoneum. The fluid characteristics can be trended to provide an indication of patient health. For example, an increase in the pressure needed to deliver the peritoneal dialysate fluid to the patient over multiple sessions could be an indication there is fibrosis building in the catheter. The system can automatically notify the health care professional of any increase in pressure. Similarly, an elevation in temperature of the filtrate removed from the patient can indicate an infection. The system can automatically notify the health care professional of an elevated filtrate temperature.

Alternatively, the color spectrum of the peritoneal dialysate filtrate can be determined using a spectroscope. A sample of filtrate from the effluent line can be removed and analyzed using an off-line or integrated spectroscope to determine the color and clarity of the filtrate. The color and clarity of the fluid can be an indication of infection in the peritoneum of the patient. In response to a change in the color spectrum of the fluid or clarity of the fluid, an alert can be issued to a health care professional indicating a possible infection.

One skilled in the art will understand that various combinations and/or modifications and variations can be made in the systems and methods depending upon the specific needs for operation. Moreover, features illustrated or described as being part of an aspect of the invention may be used in the aspect of the invention, either alone or in combination.

We claim:

1. A method for adjusting a peritoneal dialysate prescription, comprising the steps of:
   removing fluid from a peritoneal cavity of a patient;
   sampling one or more fluid characteristics of the removed fluid; and
   adjusting a peritoneal dialysate prescription based on the one or more fluid characteristics of the removed fluid;
   wherein the method uses a system having a peritoneal dialysate effluent line; at least one sensor positioned in the peritoneal dialysate effluent line; the at least one sensor configured to measure a concentration of at least one solute in a peritoneal dialysate effluent; at least one concentrate source fluidly connectable to a peritoneal dialysate flow path; and a processor; the processor configured to receive one or more fluid characteristics of a fluid removed from the peritoneal cavity of a patient from the at least one sensor and to adjust the peritoneal dialysate prescription by adjusting one or more of a dwell time, a number of cycles, and/or an osmotic agent concentration based on the concentration of the at least one solute in the peritoneal dialysate effluent.

2. The method of claim 1, wherein the step of sampling one or more removed fluid characteristics includes determining a concentration of one or more solutes in the removed fluid, determining a given volume of fluid removed from the patient, or combinations thereof.

3. The method of claim 2, wherein the solute is selected from urea, glucose, potassium, or combinations thereof.

4. The method of claim 2, further comprising the step of adjusting a number of cycles, a dwell time, an osmotic agent concentration, or combinations thereof, in response to the given volume of fluid removed from the patient.

5. The method of claim 1, wherein the fluid is from a first peritoneal dialysis cycle.

6. The method of claim 1, further comprising the step of receiving a prior history of a patient, and wherein the peritoneal dialysate prescription is adjusted based on the prior history of the patient.

7. The method of claim 6, wherein the prior history of the patient includes an osmotic agent concentration used in a prior session, an amount of fluid removed in a prior session, a dwell time used in the prior session, and a number of cycles for the prior session.

8. The method of claim 7, further comprising the step of adjusting an osmotic agent concentration, a dwell time, a number of cycles, or combinations thereof, in response to the amount of fluid removed in the prior session.

9. The method of claim 1, wherein a first amount of fluid is removed from the patient at a first time and a second amount of fluid is removed from the patient at a second time; and wherein the step of adjusting the peritoneal dialysate prescription comprises adjusting the peritoneal dialysate prescription based on a change in the fluid characteristic between the first time and the second time.

10. The method of claim 1, wherein a first amount of fluid is removed from the patient at a first time and a second amount of fluid is removed from the patient at a second time; and further comprising the step of determining a membrane transfer efficiency based on a change in the fluid characteristic between the first time and the second time.

11. The method of claim 10, wherein the fluid characteristic further comprises a clarity of the fluid, a color spectrum of the fluid, or combinations thereof.

12. The method of claim 10, wherein the step of adjusting the peritoneal dialysate prescription comprises adjusting a concentration of an osmotic agent, a number of cycles, a volume of fluid in a cycle, or combinations thereof, based on the membrane transfer efficiency.

13. The method of claim 1, further comprising the step of determining a net volume of fluid removed from the patient from the given volume of fluid removed from the patient.

14. A system for adjusting a peritoneal dialysate prescription comprising:
- a peritoneal dialysate effluent line;
- at least one sensor positioned in the peritoneal dialysate effluent line; the at least one sensor configured to measure a concentration of at least one solute in a peritoneal dialysate effluent;
- at least one concentrate source fluidly connectable to a peritoneal dialysate generation flow path; and
- a processor; the processor configured to receive one or more fluid characteristics of a fluid removed from the peritoneal cavity of a patient from the at least one sensor and to adjust one or more of a dwell time, a number of cycles, and/or an osmotic agent concentration based on the concentration of the at least one solute in the peritoneal dialysate effluent.

15. The system of claim 14, further comprising at least a second sensor configured to sense a volume of fluid removed from a patient.

16. The system of claim 14, wherein the at least one sensor is configured to sense a solute concentration of a fluid removed from a patient.

17. The system of claim 14, the peritoneal dialysate generation flow path having:
  i) a water source fluidly connectable to the peritoneal dialysate generation flow path;
  ii) one or more water purification modules fluidly connectable to the peritoneal dialysate generation flow path;
  iii) a sterilization module fluidly connectable to the peritoneal dialysate generation flow path; and
  iv) an integrated cycler fluidly connected to the peritoneal dialysate generation flow path;
  the processor configured to control the movement of fluid from the at least one concentrate source to the peritoneal dialysate generation flow path based on an adjusted peritoneal dialysate prescription by controlling one or more pumps and/or valves.

18. The system of claim 17, wherein the at least one concentrate source comprises at least an osmotic agent source and an ion concentrate source.

19. The system of claim 14, further comprising:
  i) a water source fluidly connectable to a peritoneal dialysate generation flow path;
  ii) one or more peritoneal dialysate regeneration modules fluidly connectable to the peritoneal dialysate generation flow path;
  iii) a sterilization module fluidly connectable to the peritoneal dialysate generation flow path;
  the processor configured to control the movement of fluid from the at least one concentrate source to the peritoneal dialysate generation flow path based on an adjusted peritoneal dialysate prescription by controlling one or more pumps and/or valves.

20. The system of claim 19, further comprising an integrated cycler; the integrated cycler comprising:
  (i) a cycler pump; and
  (ii) an infusion line and the peritoneal dialysate effluent line, or a combined infusion and effluent line;
  wherein the infusion line or combined infusion and effluent line is fluidly connected to the peritoneal dialysate generation flow path downstream of the sterilization module; and wherein the peritoneal dialysate effluent line is fluidly connected to the peritoneal dialysate generation flow path upstream of the one or more peritoneal dialysate regeneration modules.

* * * * *